United States Patent
Kanai et al.

[11] Patent Number: 5,327,217
[45] Date of Patent: Jul. 5, 1994

[54] APPARATUS FOR MEASURING PARTICULATE SIZE WITHOUT CONTACTING THE PARTICULATE

[75] Inventors: Kenzo Kanai, Fukui; Hiroshi Ito, Minoo; Norikane Kanai, Fukui, all of Japan

[73] Assignee: Kanai School, Inc., Fukui, Japan

[21] Appl. No.: 79,456

[22] Filed: Jun. 21, 1993

Related U.S. Application Data

[60] Continuation of Ser. No. 868,850, Apr. 16, 1992, abandoned, which is a division of Ser. No. 504,358, Apr. 3, 1990, abandoned.

Foreign Application Priority Data

Apr. 5, 1989 [JP] Japan .................................. 1-87639

[51] Int. Cl.$^5$ .............................................. G01B 11/02
[52] U.S. Cl. ..................... 356/353; 356/355; 356/357; 356/385; 356/335
[58] Field of Search ............... 356/353, 355, 357, 384, 356/385, 335–343, 238; 250/560

[56] References Cited

U.S. PATENT DOCUMENTS

| | | | |
|---|---|---|---|
| 3,518,007 | 6/1970 | Ito | 356/357 |
| 3,680,901 | 8/1972 | Rudd | 356/335 |
| 3,709,610 | 1/1973 | Kruegle | 356/355 |
| 3,797,939 | 3/1974 | Pryor | 356/335 |
| 3,851,180 | 11/1974 | Kato et al. | 250/560 |
| 4,008,704 | 2/1977 | Plocke | 356/355 |
| 4,095,898 | 6/1978 | Fulwyler | 356/338 |
| 4,157,223 | 6/1979 | Skolnick | 356/354 |
| 4,160,598 | 7/1979 | Fiester et al. | 356/121 |
| 4,201,473 | 5/1980 | Domenicali et al. | 356/360 |
| 4,511,253 | 4/1985 | Glöckner et al. | 356/385 |
| 4,882,497 | 11/1989 | Inoue et al. | 356/384 |

FOREIGN PATENT DOCUMENTS

| | | |
|---|---|---|
| 0281077 | 9/1988 | European Pat. Off. . |
| 2431107 | 1/1975 | Fed. Rep. of Germany . |
| 1407890 | 10/1975 | Japan .................................. 356/355 |
| 0103374 | 8/1979 | Japan .................................. 356/384 |
| 665480 | 5/1988 | Switzerland . |
| 2203542 | 10/1986 | United Kingdom . |

OTHER PUBLICATIONS

"Measurement of the Size and Position of Aerosol Droplets Among Holography" Dec. 1982, W. Grabowski.
Optical Engineering "A High Resolution Holographic Particle Sizing System" May–Jun. 1979, vol. 18, No. 3, Witherow.
Power Metallurgy International "Particle and Droplet Sizer" vol. 10, No. 2, May 1978.
European Search Report dated May 15, 1992.
Introduction to Fourier Optics, "Fresnel and Fraunhofer Diffraction", pp. 62–65.
SPIE, vol. 573, Particle Sizing and Spray Analysis (1985), pp. 14 & 19.
Technical Notes and Research Briefs, "Dynamic Wire Measurements by New Inspection Techniques", vol. 46 No. 2, pp. 314–315, 1969, Watkins et al.

*Primary Examiner*—Richard A. Rosenberger
*Assistant Examiner*—Hoa Q. Pham
*Attorney, Agent, or Firm*—Staas & Halsey

[57] ABSTRACT

An apparatus is described for measuring the size of a particulate, without contacting the particulate, and therefore without extra forces on the particulate. Stripped gaps of interference fringes are measured behind the particulate when a monochromatic beam is radiated on the particulate.

3 Claims, 4 Drawing Sheets

APPARATUS FOR MEASURING PARTICULATE SIZE WITHOUT CONTACTING THE PARTICULATE

This application is a continuation of application Ser. No. 07/868,850, filed Apr. 16, 1992, now abandoned; which is a division of application Ser. No. 07/504,358, filed Apr. 3, 1990, now abandoned.

BACKGROUND OF THE INVENTION

This invention relates to an apparatus of measuring particulate size without actually contacting the particulate and more particularly to a new apparatus for measuring the size of a particulate simply and rapidly based on interference fringes generated at striped gaps corresponding to the size of the particulate, when a monochromatic beam is radiated on the particulate. By using this invention, improved quality control is available for ceramic powders, magnetic recording material powders and also powder metallurgy and, moreover, it is possible to measure the size of solid state powders as well as liquid state powders, which benefits largely the industrial world.

As well known, about 200 years ago, Thomas Young advanced a theory that interference fringes can be observed at equivalent gaps and in a concentric condition caused by secondary spherical waves originating from the boundary of a subject when a beam is radiated on a subject. At that time, however, interference fringes were not obtained correctly at equivalent gaps, even when experiments were conducted based on the theory of Thomas Young, and therefore his theory was originally concluded to be in error. Thereafter, Young's theory was studied by many scholars, and finally it came to be recognized as a correct theory. However, up to now actual experiments applying the above theory have not been successful.

In view of this situation, the present inventor has performed various experiments, in a trial and error manner, in order to prove Young's theory. As a result, the inventor has found that the interference fringes appear in "shade portions" at equivalent gaps and in a concentric condition when a monochromatic beam is radiated on a particulate having a size in the range of, e.g., 100~1000 micrometers. "Shade portions" means a region which is created behind the subject on the opposite side from the light source. This region can also be called a "Geometrical Shadow Region" and is illustrated in FIG. 4.

Further, he has developed the formula mentioned below based on four elements—a gap of interference fringes ($\Delta x$), wavelength of monochromatic beam ($\lambda$), size (D) of a particulate, and the distance (Z) between the particulate and a place (e.g., screen) where the interference fringe is measured:

$$\Delta x = \frac{\lambda Z}{D}$$

From the above formula, the size (D) of the particulate is obtainable through the derived formula below:

$$D = \frac{\lambda Z}{\Delta x}$$

This invention utilizes the above-described discoveries for measuring the size of a particulate.

Thus the present invention has an object to provide a new apparatus, by which correct and rapid measuring of particulate size is available without any actual physical contact of the particulate.

The invention has another object to provide a new apparatus to obtain a value for a size of very tiny particulates, even within a range of a few micrometers.

This invention has an even further object to provide a new apparatus to improve quality control for various powder materials such as ceramic powders and so on.

Other objects and advantages of the instant invention will become more apparent from the following description taken in conjunction with the accompanying drawings, in which like reference characters designate the same or similar parts throughout the figures thereof.

SUMMARY OF THE INVENTION

This invention provides a measuring method of particulate size without any contact with the particulate. A gap of interference fringes ($\Delta x$) which occurs on a plane surface behind a particulate is measured when a monochromatic beam is radiated on the particulate, and the obtained value ($\Delta x$) is used in the formula mentioned below:

$$D = \frac{\lambda Z}{\Delta x}$$

$D$ = size of a particulate;
$\lambda$ = wavelength of monochromatic beam;
$Z$ = distance between a particulate and the place of measurement D = size of a particulate;
$\lambda$ = wavelength of monochromatic beam;
Z = distance between a particulate and the place of measurement Through the formula, the size (D) of a particulate is obtained.

BRIEF DESCRIPTION OF THE DRAWINGS

The accompanying drawings, which are incorporated in and constitute a part of the specification, illustrate embodiments of the invention and, together with the description, serve to explain the principles of the invention.

DESCRIPTION OF THE PREFERRED EMBODIMENTS

Figure 1:
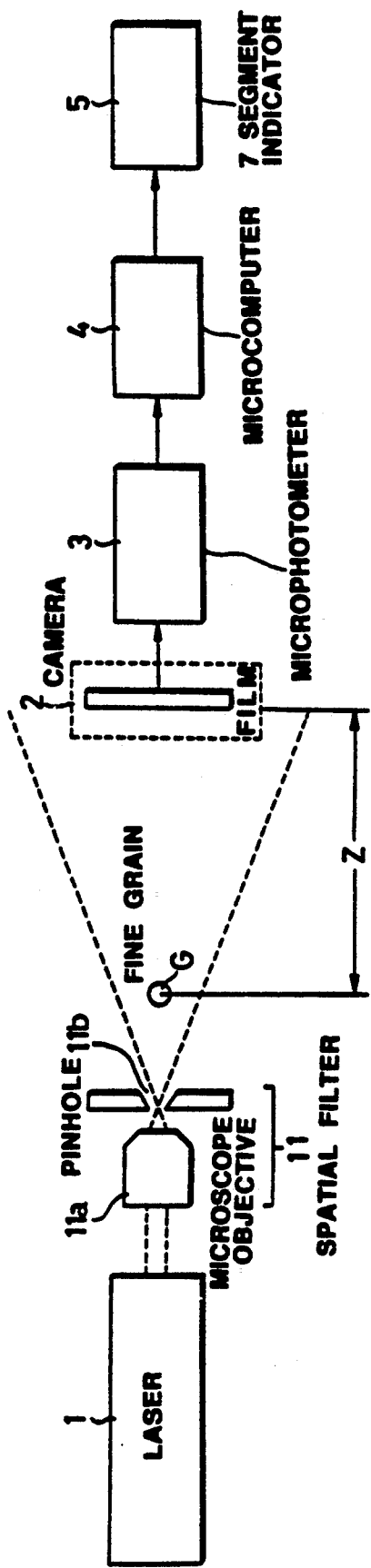
FIG. 1 is a block diagram of the apparatus according to a first embodiment of the invention.

In FIG. 1, reference numeral (1) indicates a light source in the form of, e.g., an He-Ne laser generator, for generating a monochromatic laser beam of 632.8 mm wavelength. The laser beam shines on a fine grain or particulate (G) through a spatial filter (11) equipped with a microscope objective (11a) and a pinhole (11b). The image thereof, including a shade portion created by late particulate (G), is photographed on film (21) included in a pattern recording means (2) in the form of, e.g., a lenseless camera.

In this first embodiment, the particulate (G) is merely dropped into the path of the laser beam. However, this type of drop method is not required. The drop method can be selected based on the drop speed of the subject (such as specific gravity, buoyancy, viscosity and movement) and on the sensitivity of the recording means (such as photo film, piezo-electric converter) and exposure time. For examples, a falling movement method wherein the particulate is dropped between electrodes in the chamber (wherein the particulate is of electrified quality, being electrified under a static electrical process or chemical process), or a standstill method, wherein the particulate is kept still in the air by balancing the effects of e.g., gravity, viscosity, can be used.

Reference numeral (3) indicates a measuring means in the form of a microphotometer, which reacts with light variations caused by a gap of interference fringes at the shade portion formed by the particulate (G) on the film (21). The microphotometer outputs a signal of the gap ($\Delta x$) by the changes of electric current value.

Figure 5:
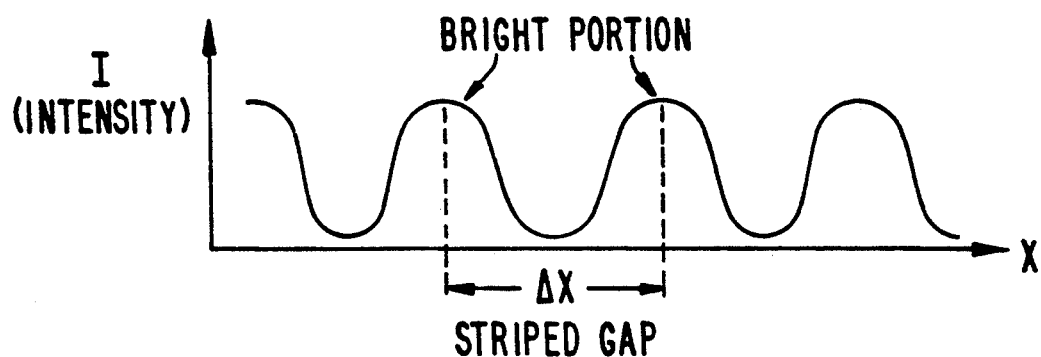
FIG. 5 is a graph comparing intensity and striped gap.

An interference fringe is an interference pattern consisting of the difference between a bright portion and a dark portion, while an interference gap consists of the difference between a bright portion and the next bright portion, as shown in FIG. 5, or else the difference between a dark portion and a next dark portion.

Then, the obtained signal ($\Delta x$) is input into a microcomputer used as a calculation means (4), where the value ($\Delta x$) is used in the following formula:

$$D = \frac{\lambda Z}{\Delta x}$$

D = size of a particulate;
λ = wavelength of monochromatic beam;
Z = distance between a particulate and the place of measurement D = size of a particulate;
λ = wavelength of monochromatic beam;
Z = distance between a particulate and the place of measurement Then, a calculation is performed and the value signal is displayed as a digital number at a display means (5) in the form of, e.g., a seven segment indicator. In this embodiment, this 7 segment indicator has seven displays which emit independently, using an LED (Light emitting Diode), a fluorescent character display tube or a liquid crystal display. The 7 segment indicator is a just one embodiment for forming an analog or digital expression of the value.

Figure 2:
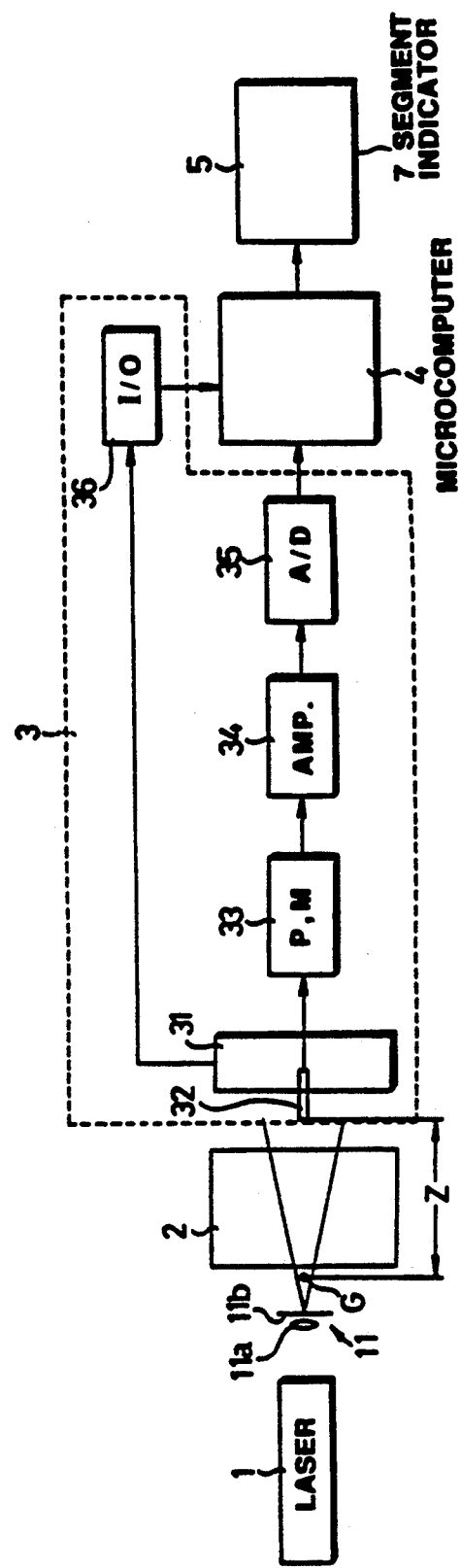
FIG. 2 is a block diagram of the apparatus according to a second embodiment.

FIG. 2 is an apparatus for a second embodiment including a photoelectric mechanism, and a measuring means (3) in the form of photographic equipment including a photomultiplier tube.

The measuring means (3) is disposed downstream in the path of the laser beam shining upon a particulate (G). The measuring means includes an optical fiber input section (32) driven and controlled by a pulse motor (31); a photomultiplier tube (33) which converts variations in light entering the optical fiber input section (32) into an electrical signal for output; an amplifier (34) which amplifies the output of the photomultiplier tube (33); an A-D converter (35) which changes the signal outputted by the amplifier (34) into a digital number; and an I-0 processor (36) which measures scanning volume of the optical fiber input section (32).

A laser beam caused by the light source (1) shines upon the particulate (G), whereon the shades of interference fringes are formed, and the shade changes are inputted into the optical fiber input section (32) and are transmitted to the photomultiplier tube (33), whereupon they are changed into a display signal by the photoelectric effect and are transmitted to the amplifier (34) where the signal is inputted into the A-D converter (35), after it is amplified to the required signal, and then is input into the calculation means (4), i.e., microcomputer. This microcomputer performs an arithmetic operation on the scanning volume of the I-0 processor (36) and on the signal transmitted through the A-D converter (35), and thus the size of the particulate is obtained correctly in an immediate manner and can be displayed at the display means or indicator (5).

Figure 3:
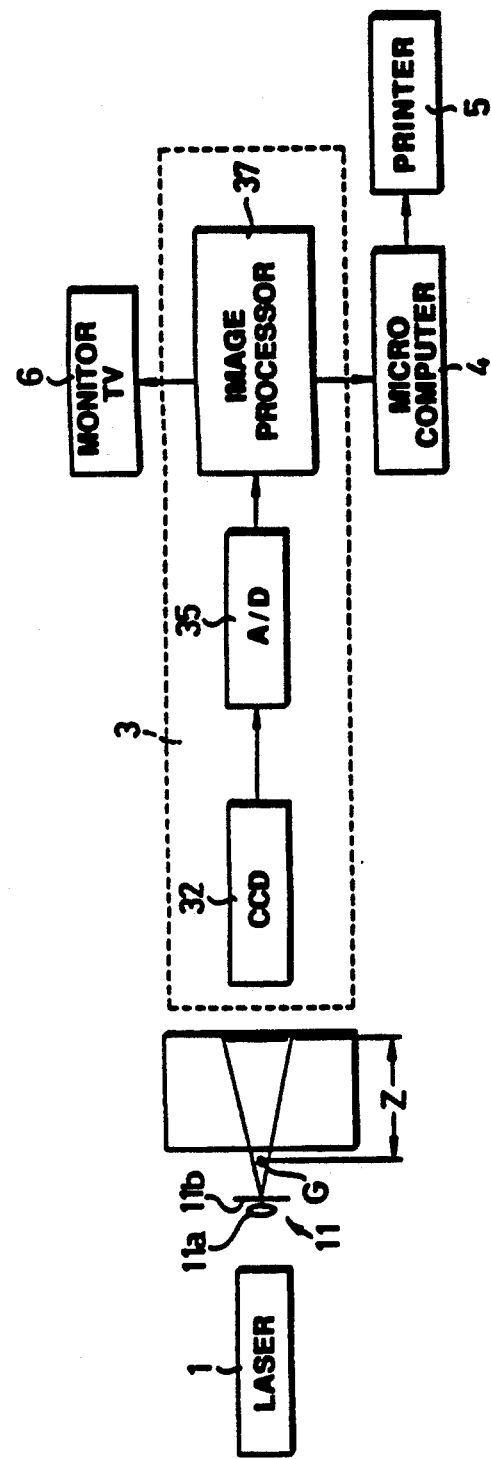
FIG. 3 is a block diagram of a third embodiment.
Figure 4:
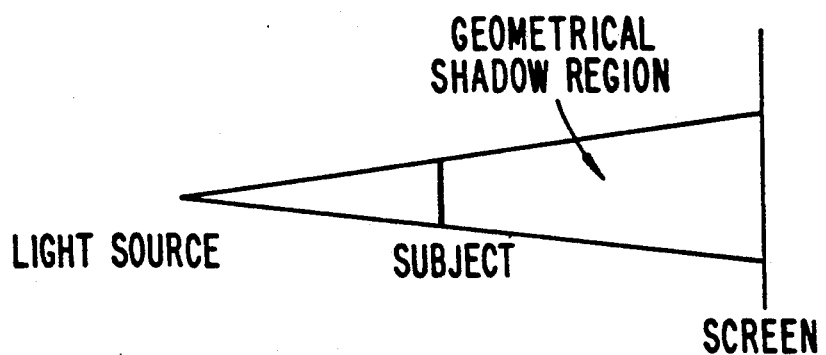
FIG. 4 is a schematic view showing formation of a geometrical shadow region.

FIG. 3 illustrates the third embodiment of this invention. In this instance, the measuring means (3) comprises a CCD image sensor (40), an A-D converter (35) and an image processor (42). The light source (1) and pattern recording means (2) are the same as in the first embodiment. The laser beam shines upon the particulate (G) and the shade changes of interference fringes are formed on the pattern recording means (2), then they are stored at the image-processor (42) via the CCD image sensor (40) and A-D converter (35), whereupon the size of the particulate (G) is calculated in the microcomputer (4). In this third embodiment the image processor (42) is adopted, which receives a clear signal representative of the interference fringes and results in the measuring of minute particulate size. A television monitor (6) can be also installed with the processor (42) in order that an actual observation of the particulate (G) can be performed in real time. As an indicator means (5), a dot printer can be used, whereas the obtained size of the particulate can be printed out accordingly.

EXPERIMENTS

A glass ball, a chrome ball and a thin graphite column, each with a size smaller than 1 mm, are prepared and used in the apparatus of the first embodiment shown in FIG. 1. A monochromatic beam with a wavelength of 632.8 nm radiated from an He-Ne laser generator (1) produces the following results on the film (21) of the camera (2): concerning the glass and chrome balls, interference fringes at equivalent gaps and in concentric condition are clearly observed around the shade portions of these objects (G). On the other hand, with regard to the graphite column, the interference fringes in the striped condition at equivalent gaps in series along the shade made by each side of the column are obtained, while the interference fringes in wave condition at equivalent gaps are also observed around the shade made by the corners of the column. These are the real interference fringes that Thomas Young advanced in his theory 200 years ago. When the inventor tried this experiment with different materials such as liquid, wood, and so on, he proved that the interference fringes depend only upon the size, and not the type of material.

All gaps of interference fringes caused by the above mentioned glass ball, chrome ball and graphite column were then read by the microphotometer (3) and a gap signal ($\Delta x$) was sent to the microcomputer (4) for calculation, and the following results were shown digitally by the 7 segment indicator:

D = Size of the particulate
Z = Distance between the particulate and the film

(1) With regard to the size of glass ball:

| Z(m) | Δx | D ± Average Error ΔD |
|---|---|---|
| 0.1 | 0.0055 ± 0.0003 | 1.15 ± 0.09 |
| 0.2 | 0.0980 ± 0.002 | 1.29 ± 0.07 |
| 0.3 | 0.1460 ± 0.007 | 1.30 ± 0.07 |
| 0.4 | 0.2000 ± 0.005 | 1.27 ± 0.05 |
| 0.5 | 0.2520 ± 0.006 | 1.26 ± 0.04 |
| 0.6 | 0.2930 ± 0.005 | 1.30 ± 0.03 |

Concerning the average error ΔD of the measured value D for the size of the particulate (= glass ball), the following formula is established:

$$\Delta D = \frac{\lambda Z}{\Delta x} \sqrt{\left(\frac{\delta 1}{\Delta x}\right)^2 + \left(\frac{\delta 2}{\Delta x}\right)^2 + \left(\frac{\delta 3}{\Delta x}\right)^2}$$

With the use of a microscope the size (D) of the particulate is measured and the result was as follows:
$(1.29 \pm 0.03) \times 10^{-3}$ m

(2) With regard to the size of the chrome ball:

| Z(m) | Δx | D ± Average Error ΔD |
|---|---|---|
| 0.1 | 0.0062 ± 0.001 | 1.01 ± 0.01 |
| 0.2 | 0.1230 ± 0.001 | 1.03 ± 0.05 |
| 0.3 | 0.1880 ± 0.009 | 1.01 ± 0.05 |
| 0.4 | 0.2400 ± 0.010 | 1.10 ± 0.10 |
| 0.5 | 0.3080 ± 0.006 | 1.03 ± 0.03 |
| 0.6 | 0.3710 ± 0.004 | 1.02 ± 0.02 |

The measurement by the microscope of the size (D) of the particulate showed the flowing results:
$(1.01 \pm 0.04) \times 10^{-3}$ m

(3) With regard to the size of the graphite column:

i. Graphite column (a)

| Z(m) | Δx | D ± Average Error ΔD |
|---|---|---|
| 0.1 | 0.0068 ± 0.004 | 0.93 ± 0.05 |
| 0.2 | 0.1360 ± 0.003 | 0.93 ± 0.05 |
| 0.3 | 0.2050 ± 0.004 | 0.93 ± 0.03 |
| 0.4 | 0.2800 ± 0.040 | 0.90 ± 0.04 |
| 0.5 | 0.3440 ± 0.005 | 0.92 ± 0.02 |
| 0.6 | 0.4150 ± 0.006 | 0.91 ± 0.02 |

The measurement by the microscope of the size (D) of the particulate showed the following results:
$(0.92 \pm 0.01) \times 10^{-3}$ m ii. Graphite column (b)

| Z(m) | Δx | D ± Average Error ΔD |
|---|---|---|
| 0.1 | 0.1110 ± 0.003 | 0.57 ± 0.03 |
| 0.2 | 0.2230 ± 0.007 | 0.57 ± 0.03 |
| 0.3 | 0.3270 ± 0.009 | 0.57 ± 0.02 |
| 0.4 | 0.4380 ± 0.009 | 0.58 ± 0.02 |
| 0.5 | 0.5600 ± 0.020 | 0.57 ± 0.02 |
| 0.6 | 0.6700 ± 0.010 | 0.57 ± 0.01 |

The measurement by the microscope of the size (D) of the particulate showed the following results:
$0.56 \times 10^{-3}$ m As explained above, the present invention realizes the practical measurement of a particulate by recording the shade portions of the particulate caused, when a monochromatic beam is radiated on the particulate, but without actual contact with the particulate which is advisable since the force of the contact could change the particulate size. This invention also enables correct measurement of the size of the particulate up to a few microns scale in its exact form regardless of the material. Therefore, the invention provides improved quality control for ceramic powders in various industrial fields.

The foregoing is considered illustrative only of the principles of the invention. Further, since numerous modifications and changes will readily occur to those skilled in the art, it is not desired to limit the invention to the exact construction and operation shown and described. Accordingly, all suitable modifications and equivalents may be resorted to that fall within the scope of the invention and the appended claims.

What is claimed is:

1. An apparatus for measuring particulate size without contacting the particulate, comprising:
   (a) means for radiating a monochromatic laser beam on a path;
   (b) spatial filter means, positioned in the path between the means for radiating and the particulate, for diverging the monochromatic beam from said radiating means and for forming behind the particulate a clear boundary diffraction interference fringe accurately inversely proportional to the particulate size, by diffracting at a boundary around said particulate, when said particulate in a measuring position is radiated by said diverging monochromatic beam; and
   (c) means for measuring the gap Δx of the boundary diffraction interference fringe and calculating the size of the particulate based on the formula $D = \lambda Z/\Delta x$, where D is the size of the particulate, λ is the wavelength of the monochromatic beam, and Z is the distance between the particulate and said boundary diffraction interference fringe.

2. The apparatus as recited in claim 1, wherein the radiating means is an He-Ne laser generator.

3. The apparatus as recited in claim 1, wherein the measuring and calculation means includes a microcomputer.

* * * * *